US006776911B2

(12) United States Patent
Citterio et al.

(10) Patent No.: US 6,776,911 B2
(45) Date of Patent: Aug. 17, 2004

(54) METHODS FOR SURFACE MODIFICATION OF SILICA FOR USE IN CAPILLARY ZONE ELECTROPHORESIS AND CHROMATOGRAPHY

(76) Inventors: Attilio Citterio, Piazza Piola, 5, Milano (IT), I-20131; Roberto Sebastiano, Vai Bramante, 133, Legnano (IT), I-20025; Cecilia Gelfi, Vai T. Grossi, 5, Monza (IT), I-20052; Pier Giorgio Righetti, Vai Archimede, 144, Milano (IT), I-20129

( * ) Notice: Subject to any disclaimer, the term of this patent is extended or adjusted under 35 U.S.C. 154(b) by 175 days.

(21) Appl. No.: 10/069,567
(22) PCT Filed: Feb. 13, 2001
(86) PCT No.: PCT/EP01/01544
§ 371 (c)(1),
(2), (4) Date: Jul. 3, 2002
(87) PCT Pub. No.: WO01/61334
PCT Pub. Date: Aug. 23, 2001

(65) Prior Publication Data
US 2002/0179532 A1 Dec. 5, 2002

(30) Foreign Application Priority Data
Feb. 18, 2000 (IT) .................................. M12000A0294

(51) Int. Cl.[7] .............................................. B01D 15/08
(52) U.S. Cl. .................... 210/635; 210/656; 210/198.2; 210/502.1; 204/451; 530/413; 530/417; 544/349; 544/401; 544/402; 544/404

(58) Field of Search ................................ 210/635, 656, 210/659, 198.2, 502.1; 544/349, 401, 402, 404; 530/413, 417; 204/451

(56) References Cited

U.S. PATENT DOCUMENTS

| 2,417,992 | A | | 3/1947 | Niederl ........................ 260/247 |
|---|---|---|---|---|
| 3,366,638 | A | | 1/1968 | Kuhnis ........................ 260/294 |
| 4,014,678 | A | | 3/1977 | Huppi et al. ..................... 71/94 |
| 4,690,749 | A | * | 9/1987 | Van Alstine et al. ......... 204/456 |
| 4,904,629 | A | | 2/1990 | Galla et al. .................. 502/164 |
| 5,391,274 | A | | 2/1995 | Shieh ....................... 204/180.1 |

FOREIGN PATENT DOCUMENTS

| DE | 836 937 | 4/1952 | ................. 544/349 |
|---|---|---|---|
| WO | WO 97/04308 | 2/1997 | ................. 204/451 |

* cited by examiner

Primary Examiner—Ernest G. Therkorn
(74) Attorney, Agent, or Firm—Young & Thompson

(57) ABSTRACT

The present invention refers to the use of novel molecules able to bind tenaciously to silica, borosilicate and silicate surfaces, and thus to modify their properties and characteristics. When applied to silica-based chromatography, it offers important advantages in all cases in which it is necessary to modulate the interaction of analytes with the stationary phase. In capillary zone electrophoresis (CZE), such compounds will eliminate or invert the electroendoosmostic (EEO) flow, greatly simplifying the analysis of negatively-charged compounds and permitting the analysis of bio(macro)molecules via the direct use of naked capillaries.

13 Claims, 9 Drawing Sheets analysis conditions: fused silica capillary, pre-treated for 5 min with a 1 mM solution of compound (1), $\phi = 50$ μm, $L_{tot.} = 60$ cm, 25 mM borate buffer, pH = 9.0, -20 kV, T = 20°C, $\lambda = 210$ nm.

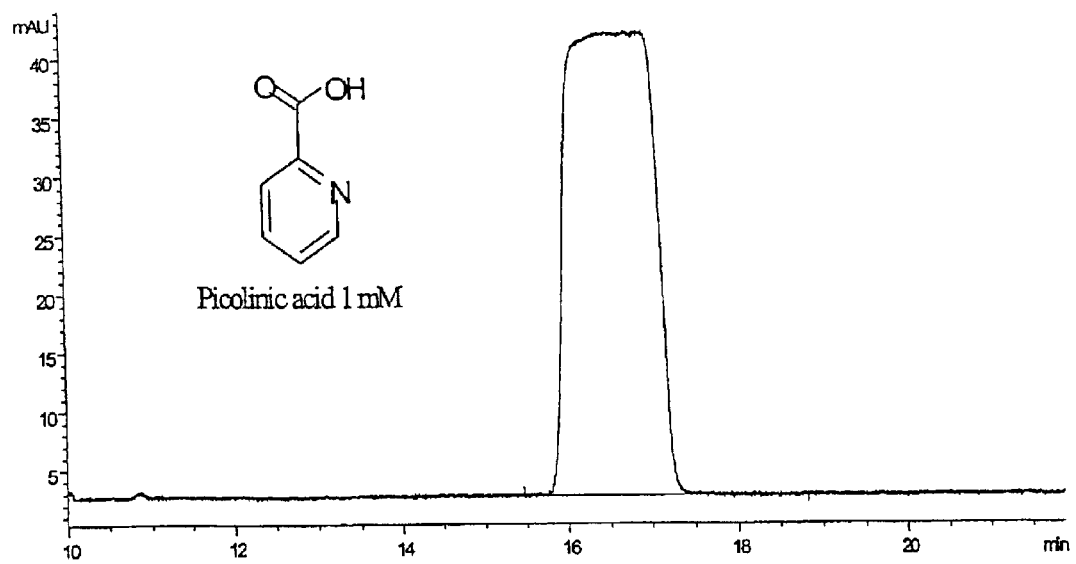
Figure 1: analysis conditions: fused silica capillary $\phi = 50$ μm, $L_{tot.} = 60$ cm, 50 mM borate buffer, pH = 9.0, + 15 kV, T = 20°C, $\lambda = 210$ nm.

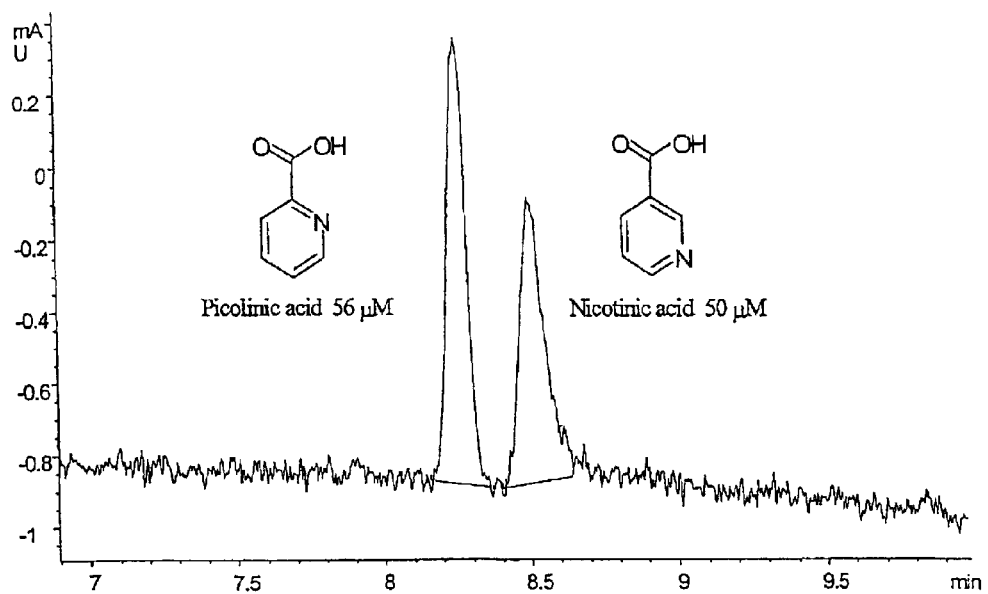
Figure 2: analysis conditions: fused silica capillary, pre-treated for 5 min with a 1 mM solution of compound (1), $\phi = 50$ μm, $L_{tot} = 60$ cm, 25 mM borate buffer, pH = 9.0, -20 kV, T = 20°C, $\lambda = 210$ nm.

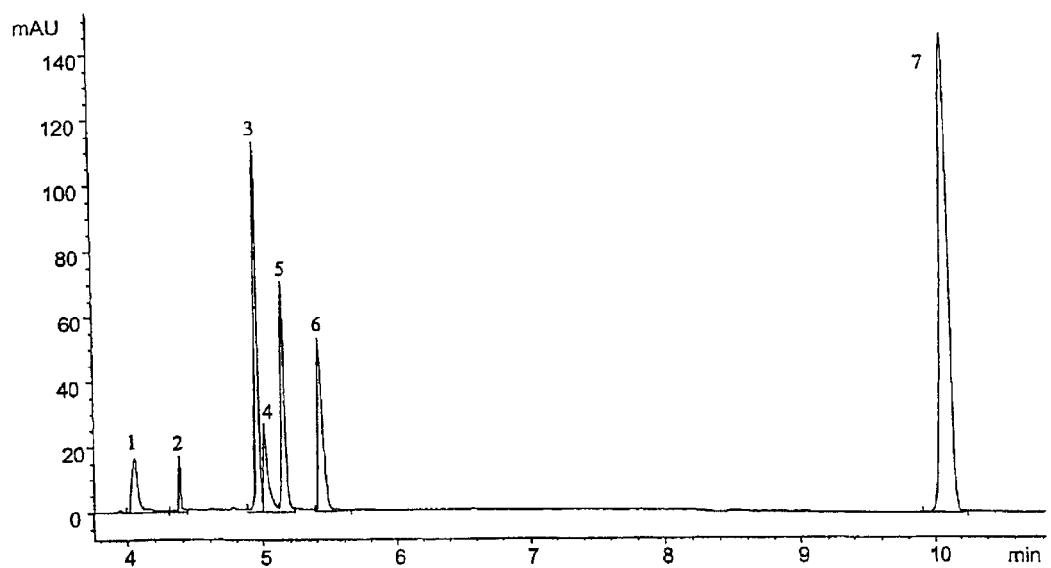
Figure 3: analysis conditions: fused silica capillary, $\phi = 50$ μm, $L_{tot} = 60$ cm, 25 mM borate buffer, pH = 8.5, - 20 kV, T = 20°C, $\lambda = 210$ nm. Analyte concentration: 0.2 mg/ml.

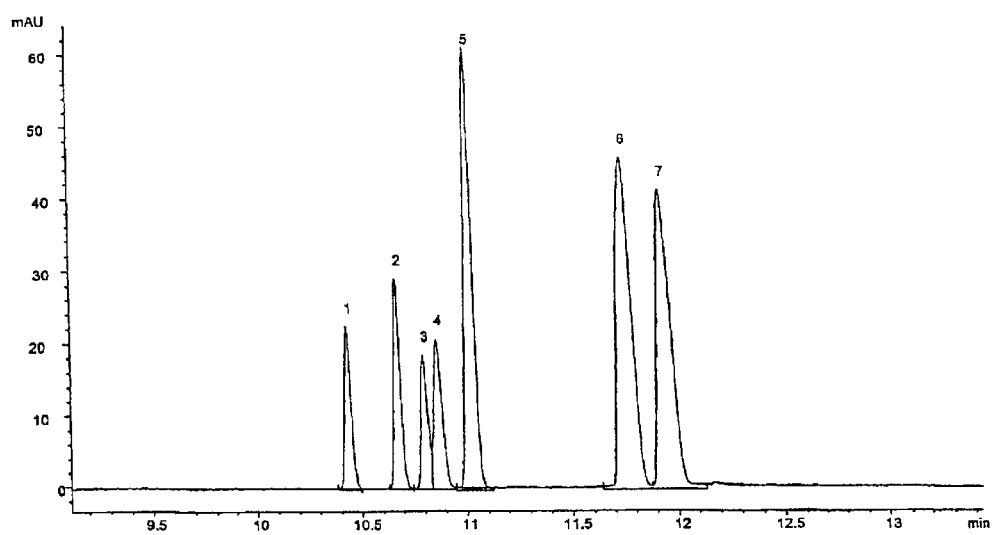
Figure 4: analysis conditions: fused silica capillary φ = 50 μm, $L_{tot.}$ = 100 cm, 25 mM borate buffer, pH = 8.5, - 25 kV, T = 25°C, λ = 210 nm. Analyte concentration: 0.14 mg/ml.

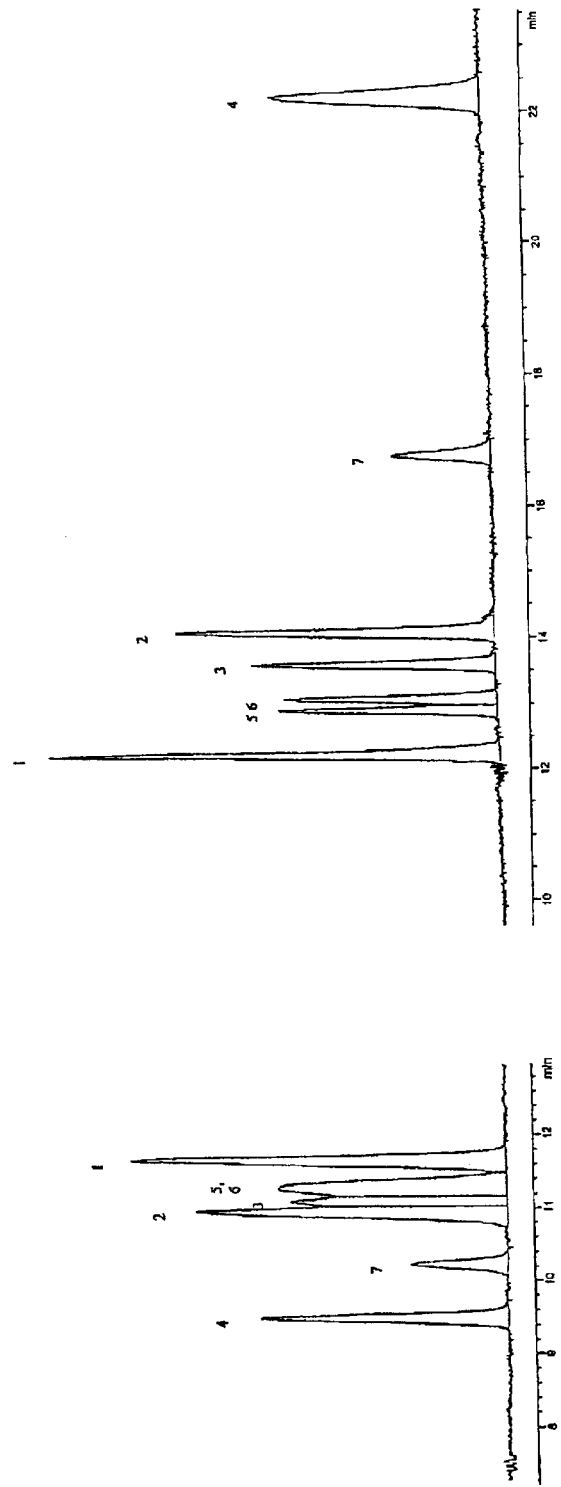
Figure 5A: analysis conditions: uncoated fused silica capillary $\phi = 50$ μm, $L_{tot.} = 50$ cm, 25 mM borate buffer, pH = 9, + 15 kV, T = 25°C, λ = 210 nm.i
Figure 5B: analysis conditions: fused silica capillary $\phi = 50$ μm, $L_{tot.} = 50$ cm, 25 mM borate buffer, pH = 9, - 25 kV, T = 25°C, λ = 210 nm.

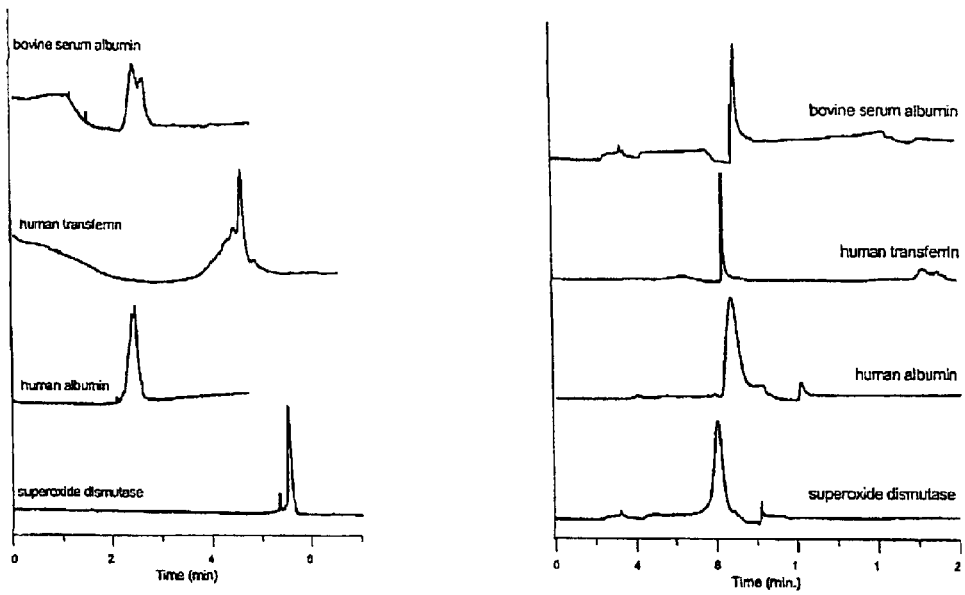
Figure 6: Separation of a number of protein markers, injected in a covalently coated (left) and in a Q-PzI treated (right) capillary, respectively. Capillary length 37 cm, 50 μm i.d.. Separation conditions were: run at 200 V/cm, sample injection by pressure for 2 sec, 5 psi/s, detection at 214 nm. In both cases the running buffer was 25 Mm Na tetraborate, Ph 9.0.

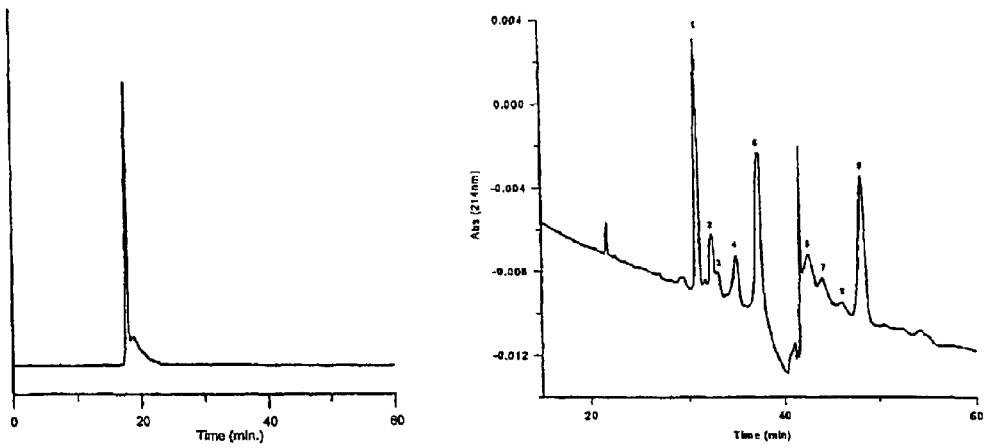

Figure 7: Separation of protein mixture with Pi ranging from Ph 3-10 (right) with QpzI treated capillary 77 cm long, 50 µm i.d.; (left) covalently coated capillary, 77 cm long, 50µ m, i.d..

Separation conditions: 250V/cm, sample injection by pressure for 5 sec, running in tetraborate buffer Ph 9.0.(1) Horse myoglobin, (2) bovine carbonicanhydrase B, (3) human carbonicanhydrase B, (4) β-lactoglobulin A, (5) soybean trypsin inhibitor, (6) lentil-lectin Pi 8.15 (7) lentil-lectin Pi 8.55, (8) lentil-lectin Pi 8.65, (9) trypsinogen

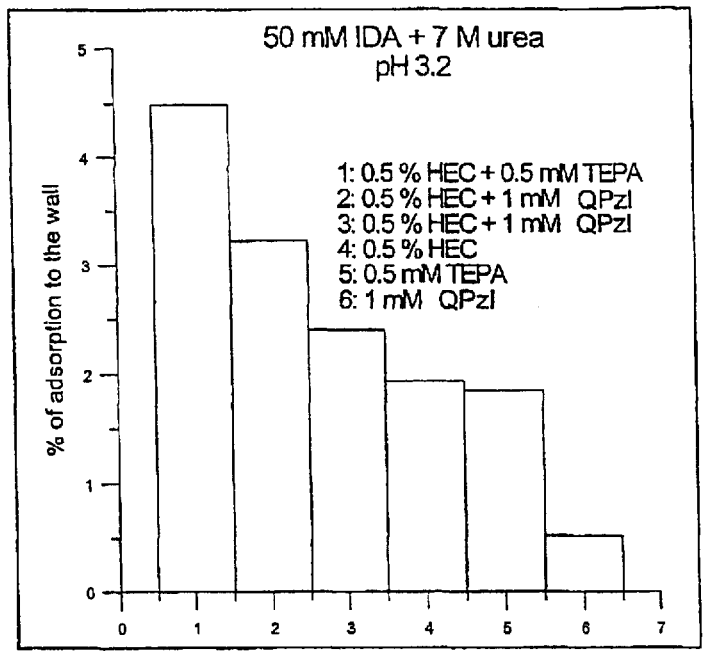

Figure 8: inhibition ability of different additives to the binding of proteins to the silica wall. The electrophoretic runs have been performed in 50 Mm IDA buffer, in presence of 8 M urea (apparent Ph of 3.2) in Waters Quanta 4000E instrument, in a 27-cm-long uncoated capillary, 50 μm ID. Sample: mixture of α and β human globin chains, 2 mg/Ml. After 10 consecutive runs, the adsorbed proteins are eluted electrophoretically in 25 Mm phosphate buffer, Ph 7, containing 60 Mm SDS and detected at 210 nm.

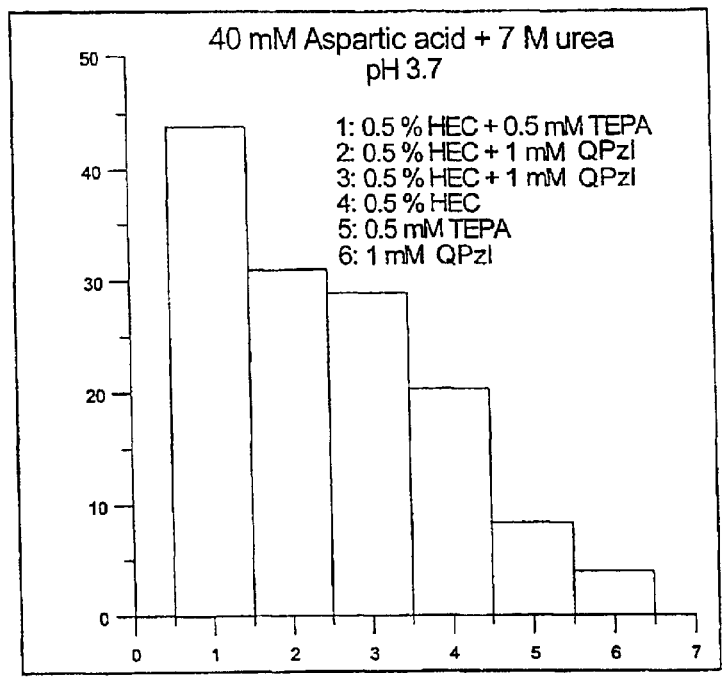

Figure 9: inhibition capability of various additives toward the adsorption of proteins to the silica wall. The electrophoretic runs have been executed in 50 mM Asp buffer in presence of 8 M urea (apparent pH 3.8) in a Waters Quanta 4000E instrument, in 27-cm-long, uncoated capillary, 50 µm ID. Buffer: a mixture of α e β human globin chains, 2 mg/mL. After 10 consecutive runs, the adsorbed proteins are eluted electrophoretically in 25 mM phosphate buffer, pH 7, containing 60 mM SDS and detected at 210 nm.

METHODS FOR SURFACE MODIFICATION OF SILICA FOR USE IN CAPILLARY ZONE ELECTROPHORESIS AND CHROMATOGRAPHY

REFERENCE TO RELATED APPLICATIONS

This application is a 371 of PCT/EP01/01544 filed Feb. 13, 2001.

The present invention refers to the use of novel molecules able to bind tenaciously to silica, borosilicate and silicate surfaces, and thus to modify their properties and characteristics. When applied to silica-based chromatography, it offers important advantages in all cases in which it is necessary to modulate the interaction of analytes with the stationary phase. In capillary zone electrophoresis (CZE), such compounds will eliminate or invert the electroendoosmotic (EEO) flow, greatly simplifying the analysis of negatively-charged compounds and permitting the analysis of bio(macro)molecules via the direct use of naked capillaries.

The fused silica is constituted of three types of ionizable silanols: isolated, geminal and vicinal. The density of such groups has been estimated of the order of 5 silanols per $nm^2$, whose average $pK_a$, value has been estimated as 6.3 (M. S. Bello, L. Capelli e P. G. Righetti, *J. Chromatogr. A* 684, 1994, 311). Thus, at any operative pH value above 2, there will be a fraction of ionized silanols, fraction which will be larger and larger at progressively higher pH values till reaching a plateau at pH ca. 10.

The EEO flow in a fused silica column is produced by the electric field and is transmitted by the drag of ions in a thin liquid layer adjacent to the silica wall. The origin of the net positive charge in this thin liquid sheath is due to the progressive ionization of silanol groups in the wall. The electric potential generated by these fixed negative charges generates a diffuse double layer (called Debye-Hückel layer) in which there exist an excess of cations as compared with anions in the buffer present in solution. When the electric circuit is closed, this excess of cations is continuously perturbed and drugged toward the negative pole (the cathode). Since the cations coordinate a number of hydration-water molecules, the continuous migration of this excess of cations generates a net water transport from the anode to the cathode, called EEO flow. This flux continues as long as the electric field is applied, since the Debye-Hückel double layer is continuously perturbed by the applied potential difference and thus it has to be continuously reformed. The EEO flow in CZE has been studied in depth, due to its fundamental importance in understanding the results of electrophoretic separations e due to its strong influence on the reproducibility of transit times. The reproducibility of the EEO flow is in fact rather modest, particularly in proximity of the $pK_a$, where the EEO vs. pH curve exhibits the highest slope. This is also due to the slow equilibration of the silica surface in changing from acidic to alkaline solutions, due, for instance, to strongly acidic or basic pH values adopted in washing the silica column after electrophoretic analysis of complex analytes, which could leave material adhering to the wall. This slow equilibration process causes dramatic variations of the EEO flux, which, in turn, could provoke poor reproducibility of the transit times of analytes, both between runs and during different days of analysis.

Per se, the EEO flux is not noxious to the electrophoretic process; on the contrary its presence is of fundamental importance when attempting separation in a single run of mixtures of anionic, cationic and neutral substances. At elevated EEO fluxes, it is possible that even negatively charged analytes, which would normally migrate to the anode, will be transported to the cathode, thus being detected at the monitoring window (in normal polarity runs the cathode is placed close to the detector). The presence of the EEO flux is of fundamental importance in methods such as electrokinetic micellar chromatography (MEKC), in which the analytes are adsorbed onto a surfactant (typically Na dodecyl sulphate, SDS). Since the surfactant micelles migrate towards the anode, but generally with lower velocities as compared with that of the EEO flux, at appropriate pH values, there is a large time window for separating both neutral and hydrophobic analytes which interact to some extent with said micelles. On the contrary, in numerous other cases, the presence of negative charges on the wall (to which the EEO flux is associated) is strongly detrimental to the electrophoretic separation. One of the most serious problems, in this case, is the adsorption of cationic analytes. Whereas such adsorption, in the case of small molecules, might be of modest entity, reversible and thus provoke only moderate losses of resolution, in the case of macromolecules, especially for proteins and peptides, this phenomenon is disastrous and could cause not only strong peak asymmetry, but even complete loss of analyte when totally and irreversibly adsorbed to the wall. Even in the case of DNA separations such EEO flow is noxious, since it causes peak asymmetry and elution of sieving liquid polymers from the capillary lumen. Over the years, many solutions have been proposed for solving this problem as reviewed in e.g., M. Chiari, M. Nesi e P. G. Righetti, in Capillary Electrophoresis in Analytical Biotechnology, P. G. Righetti, Ed., CRC Press, Boca Raton, 1996, pp. 1–36; F. E. Regnier e S. Lin, in High Performance Capillary Electrophoresis, M. G. Khaledi, Ed., Wiley, New York, 1998, pp. 683–728; G. M. McLaughlin et K. W. Anderson, in High Performance Capillary Electrophoresis, M. G. Khaledi, Ed., Wiley, New York, 1998, pp. 637–681.

Among the various solutions proposed for eliminating the EEO flux, we can recall here:

a) Variations in the type of buffer and its additives;
b) Adsorbed coatings (e.g., neutral polymers, neutral, charged or zwitterionic surfactants);
c) Covalently bound polymers, typically neutral macromolecules, such as acrylamides and celluloses, bound to the wall usually via bifunctional molecules (bridging or cross linking agents).

Covalently bound polymers have been found to be the most effective in quenching EEO flux, not only because the wall should be physically carpeted with neutral polymers, but also because, due to the anchoring of the polymers to the free silanols, there is an overall suppression of negative charges. However, such coatings are the most expensive among those offered on the market, and cannot be easily performed in individual laboratories, since good skills in organic chemistry and specialized equipment are required. In addition, this type of coating undergoes progressive deterioration during use, which calls for replacement of the capillary, this adding to the costs of analysis.

For all these reasons, dynamic capillary coatings, as obtained by additives to the background electrolyte, have been much preferred and definitely more popular among users. Among the buffer modifications there could be very simple ones, such as changes of the operative pH (e.g., at pH extremes the proteins are either repelled by the capillary, at alkaline pHs, or are not adsorbed, because the wall is neutral, at acidic pHs), or changes in the type of cation, or even the use of hydro-organic solvents, or yet strong changes in the buffer molarity (at high buffer concentrations interactions with the capillary wall are quenched or discouraged).

Each of these modifications can present some advantages, but also a number of disadvantages. A highly promising research line is the one which utilizes oligo-amines (especially tri-, tetra- and penta-amines). Oligo-amines are adsorbed to the wall via cooperative linkages, due to the presence of multiple charges on the skeleton of nitrogens and are thus able to minimize and often complete eliminate protein and peptide adsorption to the wall. Among these classes of compounds, the best ones appear to be spermine (a skeleton of four nitrogens separated by two or three carbon atoms) and TEPA (tetraethylene penta-amine) composed by a skeleton of five nitrogens separated by ethylene groups. This last molecule belongs to a large family of polyazotated compounds, both linear and branched. It would appear that the efficacy of such oligo-aminic compounds increases as a function of molecular mass as well as of the $CH_2/NH$ ratio and of the total number of ethylene groups in the molecule.

Even though the oligo-amines appear to be extremely promising both because of the ease of their use and for the efficiency of the coating, they present a common, most prominent defect: at neutral and alkaline operative pH values (the latter being the most popular for protein separations) they exhibit a drastic decrease of efficacy, since their nitrogens are progressively deprotonated, this in turn hampering the co-operative linkage to the wall (such linkage being mostly of ionic type).

Also in chromatographic processes utilizing silica beads as supports for covalent linkage of a variety of phases, silanol ionization represents a serious problem. For instance, in reversed-phase (RP)-HPLC, many companies produce silica spheres, to which hydrophobic phases, such a $C_{18}H_{37}$ ($C_{18}$ phases) or $C_8H_{17}$ ($C_8$ phases), are covalently affixed. Although reactions are carried out under conditions which should ensure full reaction of free silanols, in practice, due to steric hindrance, barely 50% of the silanol population can react (J. C. Dolan, Liquid Chrom. Gas Chrom. Int. 12, 1999, 156; D. V. McCalley, Liquid Chrom. Gas Chrom. Int. 12, 1999, 638; D. C. Leach, M. A. Stadalius, J. S. Berus & L. R. Snyder Liquid Chrom. Gas Chrom. Int. 1, 1988, 22). As a consequence, in the separation of basic compounds, peaks are strongly tailed with loss of resolution, and sometimes even total loss of analyte occurs, due to irreversible adsorption onto the silanolic phase. As a remedy, one has tried to react free silanols (the ones still not bound with $C_{18}$, $C_8$ phases etc.) with silanic agents of small size, such as trimethylchloro silane, a procedure called end capping. However, even end-capped phases still present ½ of the silanols unreacted, which means that the problems is lessened but not abolished. In order to further minimize this problem, in silica-based chromatography, already in the seventies, additives to the eluent have been proposed, able to block ionized silanols via salt bridges. Among those additives, the most popular one is triethylamine, at concentration 20–50 mM. The compounds described in the present invention, being able to bind to free silanols, are highly efficient in ameliorating chromatographic separation, as described below.

The present invention describes a novel class of molecules able to overcome all the drawbacks described above.

The compounds here claimed possess the following structural characteristics:

a) the presence of one or more quaternary nitrogens able to form ionic bonds with silanols at any operative pH value;
b) the presence of one or more basic atoms (tertiary nitrogen or oxygen, either ethereal or carbonyl) able to form hydrogen bonds or electrostatic interactions via the same heteroatoms at different pH values along the pH scale;
c) the presence of one or more alkyl chains (typically but not exclusively C-4), possessing terminal carbon atoms substituted with one or more electronegative atoms able to react with silanolic groups to such an extent as to form covalent bonds with the capillary wall.

Particularly effective appear to be quaternary ammonium salts derivatives possessing the structural formula 1, 2 and 3.

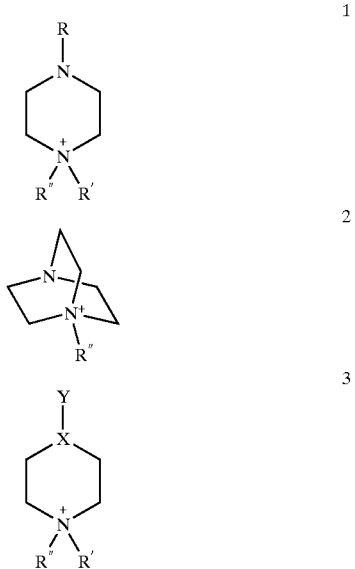

where R represents typically (but not exclusively) a $CH_3$, whereas R' and R", independently-between them, represent typically (but not exclusively) either a $CH_3$, or a group with formula $-[(CH_2)_n]-Z$, where n=2o>2, preferably 4, and Z=halogen, OH, O-alkyl (with 1–4 carbon atoms), $O-SO_2C_6H_5CH_3$, $N_3$. Compounds of relevant interest are also the heterocyclic derivatives of formula 3, where X=O, Y≠; or X=C, Y=O; or X=CH, Y=OR'''; or X=CH, Y=H, alkyl ($C_1-C_{10}$).

The preferred substituents in compounds of formula 1, 2 and 3 are R=$CH_3$, R'=$CH_3$, R"=$(CH_2)_4I$.

Other compounds covered by the present invention are molecules of type above indicated where the heterocyclic ring and/or the alkyl residues contain one or more asymmetric carbons so as to be utilized as chiral selectors.

The compounds described in the present invention can be utilized either as additives to the background electrolyte (typically at acidic pH values), or as wall modifiers introduced only during the pre-conditioning phase of the capillary (typically at neutral or alkaline pH values). Under the latter conditions, given the absence of the modifier in the background electrolyte, one obtains the unique advantage of ameliorating the signal to noise ratio, thus improving post-column techniques for analyte detection.

BRIEF DESCRIPTION OF THE DRAWINGS

FIG. 1 reports the electropherogram pertaining to the analysis of a solution of picolinic acid, at 1 mM concentration, in an uncoated capillary.

FIG. 2 gives the analysis of a mixture of picolinic and nicotinic acids at 50 micromolar concentration, performed with the procedure of wall modification described in the present invention.

FIG. 3 shows a separation obtained in CZE with the modifier QPzI as covered in the present invention.

FIG. 4 shows the electropherogram of a mixture of seven alkanoic acids analyzed with the modifier QPzI according to procedure 1.

FIG. 5A shows the electopherogram of a mixture of seven cinnamic acids analyzed with an untreated fused silica capillary.

FIG. 5B shows the electopherogram of a mixture analyzed in a fused silica capillary treated with the modifier type3.

FIG. 6 shows the profiles of five different proteins, injected in a covalently-coated vs. QPzI-treated capillary, respectively.

FIG. 7 shows the separation of a mixture of protein with pI ranging from pH 3 to pH 10.

FIG. 8 shows the ability of various additives in inhibiting protein adsorption to the silica wall.

FIG. 9 shows the ability of various additives in inhibiting protein adsorption to the silica wall.

DESCRIPTION OF THE PREFERRED EMBODIMENTS

According to the invention described so fare the synthesis of one of these families of compounds and examples on separations of both small organic molecules and macromolecules are here illustrated.

Synthesis of a Derivative Type 1 with R=CH$_3$, R'=CH$_3$ and R''=—(CH$_2$)$_4$I (OPzI)

11.4 g of N,N'-dimethylpiperazine (0.1 mol) are dissolved in 100 mL of diethylether. This solution, under stirring, is added with a mixture of 31 g 1,4-diiodobutane (0.1 mol) in 100 mL ether and let to react for 12 h. The precipitate formed (38.2 g) is filtered, washed with diethylether and dried with a vacuum pump. H-NMR (DMSO)δ(ppm): 1.71–1.88 (m, H4), 2.28 (s, 3H), 2.58–2.68 (m, H2), 2.68–2.78 (m, 2H), 3.05 (s, 3H), 3.3 (t, 2H), 3.35–3.45 (m, 6H). MS(MALDI): 296 (M+-I, 100), 169 (28). F.f 278–280° C.

EXAMPLE 1

The analysis of carboxylic acids containing heterocyclic rings with nitrogen groups, when performed in an uncoated capillary, is besieged by problems due to adsorption of such molecules to the capillary wall. The analysis of dilute solutions of such compounds is thus impossible, unless properly coated capillaries are adopted.

FIG. 1 reports the electropherogram pertaining to the analysis of a solution of picolinic acid, at 1 mM concentration, in an uncoated capillary. The wall adsorption clearly originates a broad peak, with very poor plate count.

FIG. 2 gives the analysis of a mixture of picolinic and nicotinic acids at 50 micromolar concentration, performed with the procedure of wall modification described in the present invention. In FIG. 2, it is evident how the brief capillary pre-treatment with the modifier QPzI effectively abolishes the analyte adsorption to the capillary wall, allowing thus proper quantitation of species present even at low levels, as often required in the analysis of biological fluids, in environmental analysis and in the food industry.

When operating with a new capillary, it is necessary to perform a brief pre-conditioning of the capillary, consisting in a few washing cycles, as described below, till reaching constant EEO flux values or, if required, inversion of the EEO flux.

Pre-conditioning: washing (5 bar for 2 min) with a modifier solution (2–4 mM in borate buffer, 25 mM, at pH 9.0), followed by a brief washing (5 bar for 4 min) with running buffer.

Sample analysis is performed according to the following procedure 1: washing (5 bar for 2 min) with a appropriate modifier solution (24 mM in borate buffer, 25 mM, at pH 9.0), followed by a washing (5 bar per 4 min) with running buffer, sample injection (10–20 mbar for 10 s), injection of a running buffer plug (5 mbar for 5 s).

EXAMPLE 2

Separation of a Series of Tryptophan Metabolites

The Formulae of the Various Analytes are the Following:

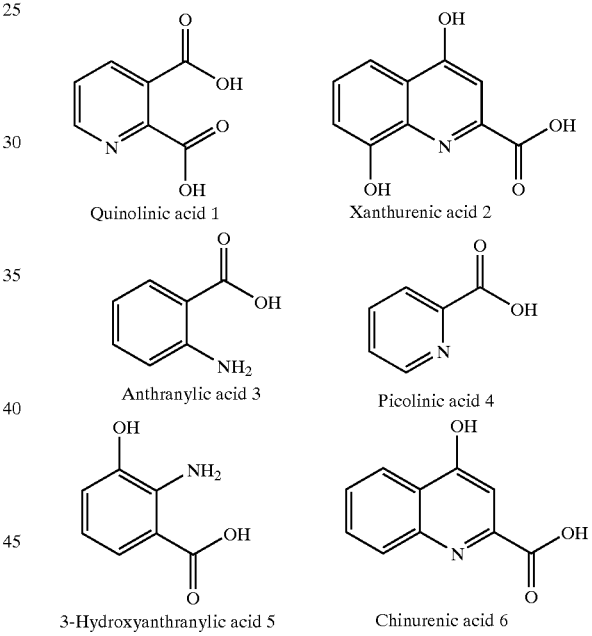

Quinolinic acid 1
Xanthurenic acid 2
Anthranylic acid 3
Picolinic acid 4
3-Hydroxyanthranylic acid 5
Chinurenic acid 6

FIG. 3 shows a separation obtained in CZE with the modifier QPzI as covered in the present invention. The analysis of the mixture is performed according to procedure 1, thus in the absence of the modifier in the running buffer. One should note the excellent separation of all six compounds in the mixture, coupled to very short analysis times (<6 min). It has not been possible to obtain such results in an uncoated capillary both due to unfavorable EEO flow and to adsorption of analytes.

Also the use of conventional oligoamines (spermine and TEPA) has not given any appreciable result. In this particular case the EEO is inverted, due to an excess of positive charges present in the piperazine bound to the silica wall. This flux inversion has been verified via the elution of a neutral marker (compound No. 7: acrylamide), eluted in ca. 10 min

EXAMPLE 3

Separation of Arylalkanoic Acids

The formulae of the various analytes are the following:

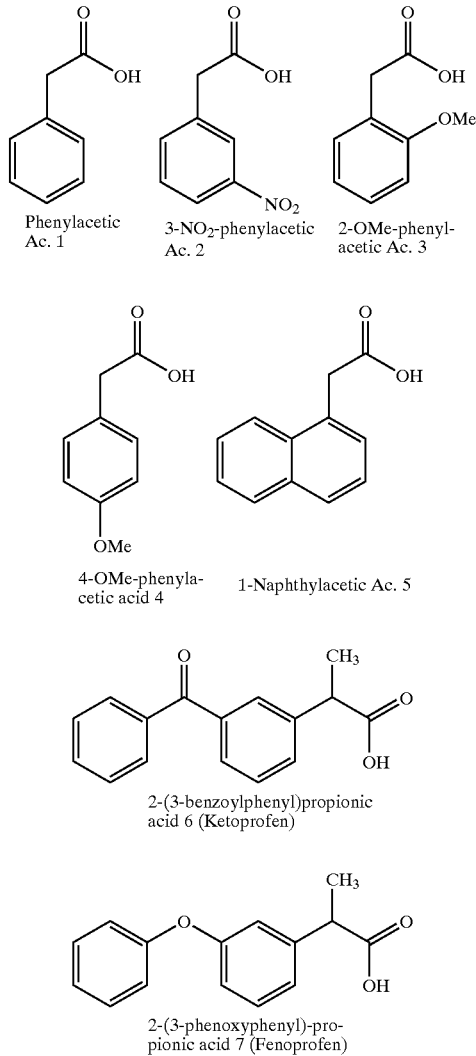

FIG. 4 shows the electropherogram of a mixture of seven alkanoic acids analyzed with the modifier QPzI according to procedure 1.

Also in this case no separation has been possible with either coated capillaries or with background electrolytes containing conventional oligo-amines (e.g., spermine, TEPA), alone or in a mixture. It is believed, in fact, that the separation of FIG. 4 has been made possible by the interaction of the analytes with the piperazine adsorbed to the wall. In this case, thus, the piperazine acts by both modulating (or inverting) the EEO flux and by becoming an active player in the separation process, due to its interaction with some analytes.

EXAMPLE 4

Separation of Cinnamic Acids

The formulae of the various analytes are the following:

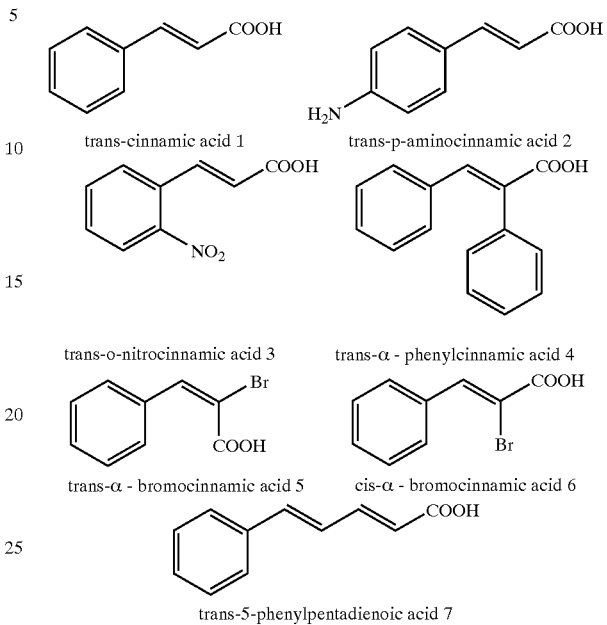

FIG. 5A shows the electropherogram of a mixture of seven cinnamic acids analyzed with an untreated fused silica capillary. It is evident the poor separation of the compound 2, 3, 5 and 6 that, on the contrary, can be well resolved using a capillary treated with the modifier type 3 (X=C, Y=O, R'=$CH_3$ and R"=$(CH_2)_8$I in according with the procedure 1 (FIG. 5B).

EXAMPLE 5

Separation of Proteins at Alkaline pH

These separations are of great interest, since at this operative pH (pH 9.0) proteins are kept in a native state. FIG. 6 shows the profiles of a five different proteins, injected in a covalently-coated vs. a QPzI-treated capillary, respectively. In the case of protein separations performed in covalently-coated capillaries, the running time are longer than observed in QPzI-treated capillaries and the peaks are broad, possibly due to diffusion, whereas the peak areas remain substantially the same, indicating the absence, or at least the same sample adsorption, to the wall.

The separation of a mixture of protein with pI ranging from pH 3 to pH 10 is shown in FIG. 7. It can be appreciated that the separation occurs according to the protein mobility and EOF. The first protein eluted is thus the moderately alkaline horse myoglobin acidic and basic band, then the acidic one which the mobility is influenced by the positive charge docked into the wall. The last group of protein is represented by the most alkaline ones, first the lentil lectins with pIs ranging from pH 8.15 to 8.65, just before the neutral marker, and then trypsinogen (pI 9.5) which overlaps with the neutral acrylamide marker. Peak identification was performed by direct spotting of the pure protein into the calibration pI mixture. FIG. 7 shows the same protein mixture injected in a covalently coated capillary (left); in this case a single peak representing the 9 proteins is obtained, indicating that interactions between the modified wall and proteins are important not only in avoiding absorption but in playing an active in the separation process.

EXAMPLE 6

Separation of Proteins at Acidic pH

These separations are of interest because, in principle, they can be performed in uncoated capillary, in the absence of any modifier, due to the absence of ionization of silanols at pH values of ca. 2.0–2.5.

However, at such strongly acidic pH values, it is to be expected that proteins will be denatured and will loose their tridimensional structure. Thus, it is better to ensure that this process will be brought to completion and therefore such analyses are typically performed in presence of denaturing/solubilizing agents, such 8 M urea. In turn, in 8 M urea solutions, the apparent pH value of the solution increases by about 1 pH unit, thus rendering quite real the risk of adsorption of proteins and peptides to the silica wall. FIG. 8 shows the ability of various additives in inhibiting protein adsorption to the wall (a mixture of α e β human globin chains) in an amphoteric, isoelectric buffer composed of 50 mM imino diacetic acid (IDA). The pH of this IDA solution is of 2.3 (pH=pI), but the addition of 8 M urea (necessary for keeping in solution the globin chains) raises the apparent pH value to ca. 3.2. It is seen how various additives, either alone or in combination, have inhibition powers ranging from ca. 95 to 98%. Only the presence of QPzI in solution (1 mM) is able to reduce protein adsorption to barely 0.5%.

In all these separations, the dynamic modifiers must always be present in solution, even in the background electrolyte during the run. This does not apply to the piperazine modifier if the capillary is first conditioned at alkaline pH values (pH 9.0) and then equilibrated in the low pH buffer. At higher pH values, in isoelectric Asp buffer (apparent pH 3.8 in 8 M urea) the situation readily deteriorates: in presence of some additives, the amount of globin chains bound to the wall reaches extremely high values, as high as 45% of the initial, injected amount. Only in presence of 1 mM piperazine alone this value is reduced to only 3% (FIG. 9). It is thus demonstrated that the piperazine additive not only can be used very efficiently along the entire pH scale for electrophoretic separations, but also that it is by far the most efficient additive in inhibiting interaction and adsorption of macromolecules to the silica wall.

What is claimed is:

1. Compounds able to modify silica surfaces and/or to inhibit or inverting the EEO flow in capillary electrophorotic separations, characterized by the following functional groups: a) one or more quaternary nitrogens; b) one or more basic atoms; c) one or more % $C_2$–$C_5$ alkyl chains containing at the end a carbon atom substituted with one ore more electronegative atoms,
said compounds optionally containing asymmetry centers.

2. Compounds as claimed in claim 1, wherein the basic atoms according to b) are selected from the group consisting of tertiary nitrogen or oxygen, either ethereal or carbonyl, and the alkyl chains according to c) are $C_4$-alkyl chains.

3. Compounds as claimed in claim 2, of formula 1 and 2,

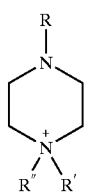

1

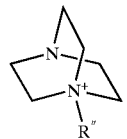

2 wherein R is a $C_1$–$C_4$ alkyl group, and R' and R'' are independently a ($C_2$–$C_4$) alkyl group or a group of formula $[(CH_2)_n]Z$, where n=3–6 and Z is halogen, hydroxy, ($C_1$–$C_4$) alkoxy, p-toluenesulphonyloxy or $N_3$.

4. A compound of formula 1 as claimed in claim 3, wherein R and R' are $CH_3$ and R'' is —$(CH_2)_4$—I.

5. A method of separation of oligonucleotides and DNA fragments comprising separating said oligonucleotides and DNA fragments with capillaries treated with the compounds of claim 3 in both conventional buffers and amphoteric, isoelectric buffers, said buffers being either acidic, neutral, or alkaline.

6. A method of separation of small molecules able to interact with the capillary wall or whose separation might be hampered by the EEO flow of non-conditioned capillaries comprising separating said small molecules able to interact with the capillary wall or whose separation might be hampered by the EEO flow of non-conditioned capillaries with capillaries treated with the compounds of claim 3.

7. A method of chiral separation comprising separating compounds with capillaries treated with the compounds of claim 3.

8. A method of chromatographic separation comprising separating compounds with the compounds of claim 1 utilizing silica-based material.

9. A method of chiral chromatographic separation comprising separating compounds with either spheres or silica material treated with the compounds of claim 1.

10. A method of electrophoretic separation of molecules comprising separating molecules with compounds of claim 1 coated on either glass or borosilicate surfaces as used in nanotechnologies.

11. The method of claim 10, wherein the coated surfaces include chips used in hyphenated techniques, said chips being interfaced with chromatographic column, with either mass detectors or other separation/detection devices, including two-dimensional separation devices.

12. A method of separation of proteins and/or peptides comprising separating said proteins and/or peptides with capillaries treated with the compounds of claim 1 at any value of the pH scale necessary for optimizing such separations.

13. A method of separation of proteins and/or peptides comprising separating said proteins and/or peptides with capillaries treated with the compounds of claim 1 in both conventional buffers and amphoteric, isoelectric buffers, said buffers being either acidic, neutral, or alkaline.

* * * * *